United States Patent [19]

Venghiattis

[11] 4,125,225

[45] Nov. 14, 1978

[54] CORROSION-FREE NEBULIZER

[75] Inventor: Alexis A. Venghiattis, Houston, Tex.

[73] Assignee: The Perkin-Elmer Corporation, Norwalk, Conn.

[21] Appl. No.: 634,587

[22] Filed: Nov. 24, 1975

Related U.S. Application Data

[63] Continuation of Ser. No. 122,570, Mar. 1, 1971, abandoned.

[51] Int. Cl.² .............................................. B05B 7/30
[52] U.S. Cl. .................................. 239/338; 239/346; 239/DIG. 19
[58] Field of Search ............... 239/337, 338, 424, 602, 239/DIG. 19, 340, 327, 346

[56] References Cited

U.S. PATENT DOCUMENTS

| | | | |
|---|---|---|---|
| 1,150,238 | 8/1915 | Winbray | 239/338 |
| 3,516,771 | 6/1970 | Rendina | 239/338 X |
| 3,525,476 | 8/1970 | Boling et al. | 239/338 |
| 3,580,510 | 5/1971 | Batlas | 239/338 X |

FOREIGN PATENT DOCUMENTS 257,646  3/1973  Fed. Rep. of Germany ........... 239/338

Primary Examiner—Joseph F. Peters, Jr.
Assistant Examiner—Michael Mar
Attorney, Agent, or Firm—Salvatore A. Giarratana; Francis L. Masselle; John D. Crane

[57] ABSTRACT

A pneumatic nebulizer of the type used for aspirating a fine spray of a liquid analytical sample into the sample burner flame of an atomic absorption spectrophotometer or the like. The nebulizer comprises an atomizing venturi nozzle formed of corrosion-resistant material, the nozzle including a monolithic flexible tube having one end extending to a sample source and its other end terminating coaxially within an apertured nozzle member to define therewith an annular orifice through which high velocity gas flow occurs to aspirate sample liquid from the other end of the tube.

4 Claims, 1 Drawing Figure

U.S. Patent      Nov. 14, 1978      4,125,225
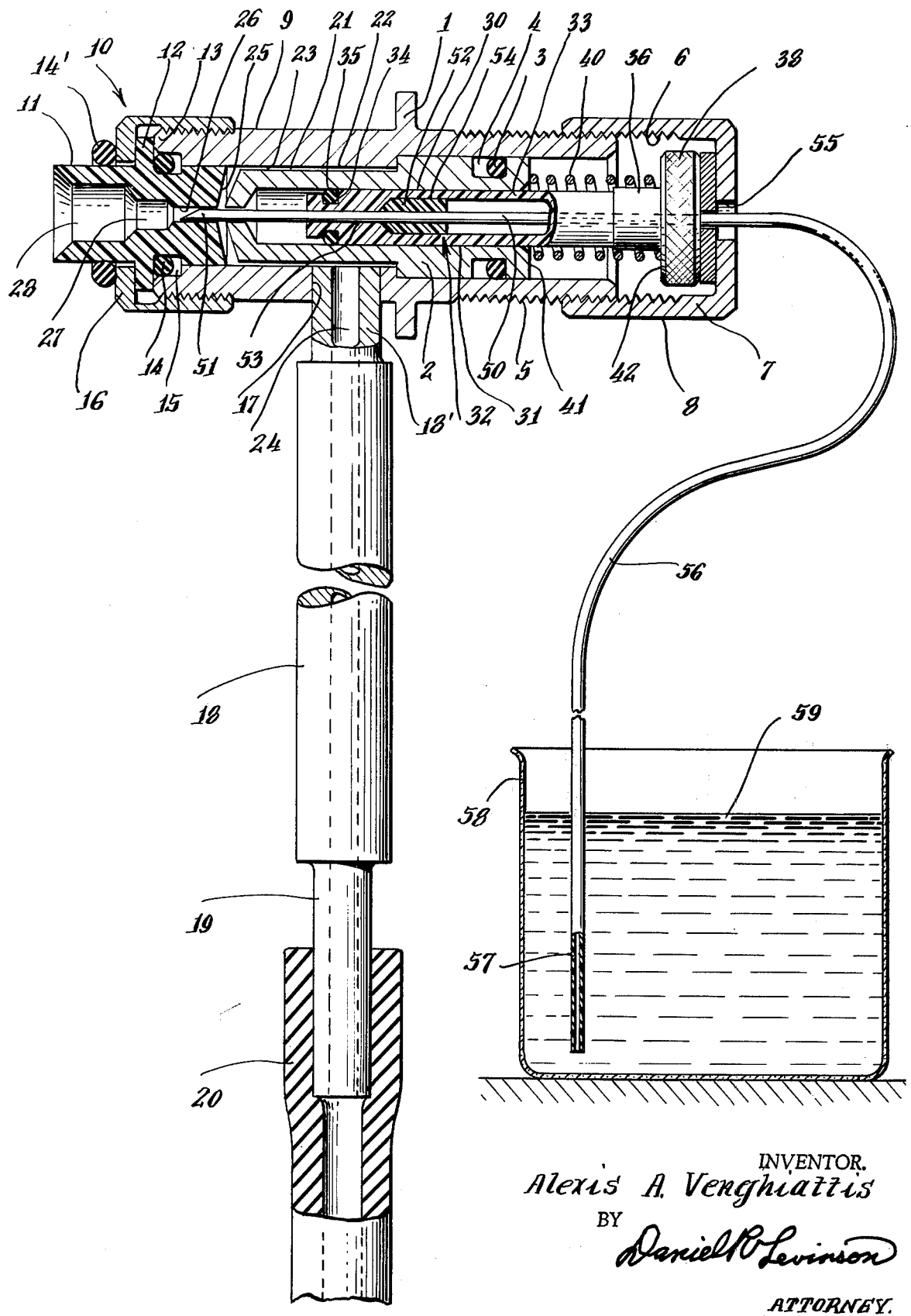
INVENTOR.
Alexis A. Venghiattis
BY
Daniel R. Levinson
ATTORNEY.

CORROSION-FREE NEBULIZER

This is a continuation of application Ser. No. 122,570 of Alexis A. Venghiattis filed Mar. 1, 1971, now abandoned.

This invention relates to nebulizers for forming, by means of an aspirating gas passing through a venturi restriction, a fine spray from a liquid at the tip of a needle-like liquid supply tube. Such nebulizers are utilized to form such a fine spray of an originally liquid sample solution for introduction into a mixing or spray sample of a burner of an atomic absorption spectrometer, wherein a gaseous fuel is added and the resulting mixture burned so as to form a flame containing atomic particles of the typically metalic sample elements of interest. The present invention is distinguished functionally by its ability to nebulize corrosive sample solutions, and structurally by the fact that the (artificial resin) capillary tube usually utilized to supply the solutions to one end of a metallic needle, the opposite end of which acts as the nebulizing tip, is instead passed directly into the throat of the venturi restriction, thereby eliminating the need for such a metal needle. Additionally, the surfaces of the device forming the venturi restriction in the immediate vicinity of the atomizing tip of the capillary are also made of a corrosive-resistant artificial resin, thereby avoiding corrosion by the fine spray of these parts.

In atomic absorption spectroscopy (see, for example, U.S. Pat. No. 2,847,899 to Walsh), the elements of interest are caused to intercept a radiation beam while the elements are in their atomic state, and a measurement of the absorption at a characteristic resonant spectral line of a particular element yields a measure of the concentration of the element in the original sample solution. At present, the most common technique for introducing a liquid sample (which typically is a solution containing the element of interest) is by aspirating the liquid by a rapidly-moving current of gas (for example, air) from the tip of a small diameter needle-like tube supplied by the sample solution. The rapidly-moving gas, typically travelling through a venturi restriction, causes the liquid to be converted into a fine spray; this mixture of gas and fine liquid spray is then mixed with a gaseous fuel in the spray-chamber of a burner and then ignited (typically at an elongated slot of the burner), so as to form in the path of the test radiation beam of the spectrophotometer a substantial quantity of the element of interest in its atomic state. When the radiation beam contains at least one spectral line corresponding to a resonant line of the atomic element of interest, a measurement of the intensity and therefore the relative absorption of such a line yields a direct measure of the original concentration of the element of interest. Both the sensitivity and the stability of the absorption and therefore the precision of the measured concentration of the element of interest is affected by the efficiency and constancy of the nebulizer in converting the liquid sample into a fine spray, the element of interest in the droplets of which are subsequently converted to their atomic state by the temperature of the flame formed.

The essential elements of a nebulizer of the type described above include: a means, typically a flexible capillary tubing, for bringing the sample solution to the nebulizer assembly; a sample-carrying needle-like tube (previously typically a metallic needle of the type used in hypodermic syringes) for introducing the sample solution into the nebulizer and having its tip within the throat of a venturi restriction; and means for conveying a gas (such as air) including means for forming the venturi restriction in which the actual nebulizing of the liquid occurs. One example of such a prior nebulizer or atomizer (having the desirable characteristic of allowing adjustment and interchangeability of the needle-like tube) is shown and described in the Davies et al article entitled, "An Adjustable Atomizer for Atomic Absorption Spectroscopy" in Volume 42 of the *Journal of Scientific Instruments* (November, 1965) on pages 816 and 817.

The present invention differs from such prior atomizers or nebulizers, including some that are otherwise extremely similar structurally to the exemplary embodiment, primarily in avoiding the use of a separate (metallic) needle-like tube as the sample-carrying part at which the actual nebulizing occurs. In the present nebulizer, the at least somewhat flexible capillary tubing from the sample supply continues right through the nebulizing assembly into the throat of the venturi restriction, so that the tip of the continuous capillary tubing itself is acted on to form the nebulized spray. This allows corrosive solutions to be directly sampled as long as the capillary tubing is itself a corrosive resistant material (for example, the artificial resin polymer of tetrafluoroethylene, commercially available under the registered trademark "Teflon"), this integral construction eliminates clogging effects previously experienced at the connection between the capillary tubing and the previously utilized metallic needle, especially with concentrated solutions, and eliminates splitting of the tubing by the needle at this connection. The important discovery that in practice the exact centering of the liquid delivering tip within the venturi throat is not necessary, where workers in this art previously believed it to be critical, has allowed the elimination of the separate rigid metallic needle previously utilized, thereby obtaining the three advantages just noted. Preferably, the other parts (forming the venturi restriction and final discharge opening of the nebulizer) coming into contact with the nebulized sample spray are also made of a corrosive-resistant material (for example, that type of artificial resin which is a polymer of chlorotrifluoroethylene sold under the trademark "Kel-F" by the Minnesota Mining and Manufacturing Corporation) to avoid deterioration.

An object of the invention is the provision of an improved nebulizer of the type described above, which is resistant to even highly corrosive sample solutions.

Another object of the invention is provision of such nebulizer which is substantially immune to clogging of the sample delivery tubing even when the solution is relatively highly concentrated as to the total amount of material other than the solvent contained therein.

Other objects, advantages, and features of the invention will become obvious to one skilled in the art from the single exemplary embodiment described hereinafter in conjunction with the drawing, in which:

The sole FIGURE is a cross-section through a nebulizer incorporating the improvements according to the invention.

DETAILED DESCRIPTION

In the drawing, the nebulizer includes a generally tubular main housing 1, inside of which is positioned a generally sleeve-shaped insert 2; a sealing "O" ring 3 is positioned in a relieved portion or groove 4 of the larger diameter, right-hand part of insert 2 so as to form a gas-tight seal between housing 1 and insert 2. The right-hand or rear portion of the outside of housing 1 is provided with screw threads as indicated at 5, which cooperatively engage internal screw threads 6 of a manually moveable cap 7, the external surface of which, as at 8, is preferably knurled. The left-hand or exit end of housing 1 is also provided with screw threads as at 9 for cooperating with a similarly internally threaded closure cap 10, which attaches the venturi member 11 to the left-hand end of the housing. In particular, the venturi member 11 is provided with an angular flange 12 which is held between the left-hand end 13 of the housing and the facing interior surface of the closure cap 10. A second "O" ring 14 is provided in mutual recesses (as at 15) of the interior and exterior surfaces, respectively, of housing 1 and venturi insert 11, so as to provide a gas-tight connection between these surfaces. Another "O" ring 14' is provided on the exterior surface of venturi member 11, which "O" ring also contacts the left-hand surface 16 of the closure cap 10 so as to provide a seal between venturi 11 and cap 10. Venturi 11 is preferably made of a corrosive-resistant artificial resin such as the commercially available material previously mentioned sold under the trademark "Kel-F".

The main housing 1 is provided near its center with a radial bore 17, in which generally tubular pipe 18 is premanently fixed in a gas-tight manner (as by press-fitting in bore 17 the reduced diameter upper end portion 18' of pipe 18). The lower end 19 of pipe 18 is of reduced external diameter so as to provide a connection for a source of compressed gas (e.g., air or nitrous oxide) by means of conventional rubber tubing 20 or the like. As may readily be seen, the exterior cylindrical surface 21 of the left-hand half of insert 2 has a lesser diameter than the corresponding internal cylindrical surface 22 of the left-hand part of housing 1, so as to form an annular passage 23 for the gas entering through the central channel 24 of pipe 18. This gas therefore flows toward the conical-shaped right-hand surface 25 of venturi member 11 and thence through the restricted venturi throat 26 thereof, before reaching the stepped wider openings 27 and 28, which act to spread or diffuse the gas (and the nebulized liquid, as will appear hereinafter).

The cylindrical interior surface 30 of insert 2 slideably supports the cylindrical external surface 31 of the liquid supply assembly referenced generally 32. The main element of this assembly is a generally tubular-shaped element 33 (preferably, but not necessarily, made of a corrosion-resistant artificial resin, such as the previously described trademarked "Kel-F" material), which has an annular external recess at 34 for holding an "O" ring 35 for forming a seal between the external surface of element 33 and the internal surface 30 of insert 2. The right-hand end of element 33 has a stepped enlarged diameter portion 36 and a further enlarged portion or end flange 38. A spring 40 bears against the right-hand surface 41 of insert 2 and the left-hand surface 42 of this flange 38, therefore tending to urge element 33 to the right (since engaging shoulder portions formed by a change in diameter of parts of insert 2 and housing 1, as shown at 43, arrest any leftward motion of insert 2). A washer 44 of low friction material relative to the material of element 33 and/or knurled cap 7 is positioned between these two elements so as to facilitate relative rotation therebetween. Therefore, manual turning of the knurled cap 7 moves the entire liquid supply assembly 32 longitudinally (i.e., along a horizontal line in the drawing) within insert 2 without causing rotation for all practical purposes, of the assembly 32 in general and element 33 in particular.

Except for the material (corrosive resistant artificial resin) of the venturi member 11 (and preferably the liquid supply assembly element 33) the structure so far described or at least substantially the same structure has been previously utilized in nebulizers. In contradistinction to such existing nebulizers the other main component of the liquid supply assembly within the nebulizer is a capillary tubing 50, rather than a (metallic) needle. In particular, this capillary tube 50 is preferably a continuous capillary tube (of the same general type previously used to bring the liquid sample to the previously utilized needle) and may be, for example, 0.033 inch external diameter, a substantially uniform 0.015 inch internal diameter tubing of a corrosive-resistant artificial resin, such as the polymer of tetrafluoroethylene commercially available under the registered du Pont trademark "Teflon". The extreme left-hand tip 51 of this tubing is preferably cut at approximately a 30° angle as measured from the horizontal, after an adjacent portion has been securely bonded within the interior of element 33 as generally indicated at 52 (prior to assembly of the components of the whole nebulizer). Preferably a bonding material such as an epoxy resin glue (such as Armstrong epoxy adhesive #12 sold by Armstrong Products Co., Inc.) is applied between the tubular interior surface of element 32 and the roughened (as by etching, e.g., with the etching solution comprising alkali metals in a liquid hydrocarbon carrier, sold by Joclin Manufacturing Co. of Wallingford, Conn. under the trade name "Fluorobond") exterior surface of tube 50 both along part of the small diameter portion 53 and the immediately adjacent larger diameter portion 54 of element 33, so that the latter securely holds tubing 50. The continuous tubing 50 leaves the right-hand end of the nebulizer (through an appropriate opening 55 in knurled cap 7) and continues uninterruptedly as indicated by continuous length 56 to end 57 engaging the source of the sample liquid, schematically illustrated as a beaker or similar container 58 containing the liquid sample at 59. It is again emphasized that tubing 50 is a continuous corrosive-resistant single tube all the way from its aspirated left-hand tip 51 to the end of 57 actually engaging the liquid sample supply.

OPERATION

Since the nebulizer of the invention operates in a manner very similar to prior nebulizers, only a brief description of the operation appears necessary, except for the specific points of differences between the present nebulizer and known ones. As in such prior nebulizers, the compressed gas entering through channel 24 in pipe 18 will proceed through annular passage 23 into the restricted throat 26 of the venturi. Within this throat the gas is travelling quite rapidly and at relatively high pressure so as to effectively suck the liquid at the tip 51 along with the rapidly moving gas, at the same time causing the liquid to be broken up into extremely small droplets so as to form a mixture of gas and a fine liquid spray or mist, which passes through the openings 27 and 28 acting to spread or diffuse this gas and liquid mist mixture. As is well known, the left-hand end of the device will feed into a burner chamber wherein another gas (e.g., the fuel) will be added and mixed with the liquid mist and original gas (e.g., oxidant) provided by pipe 18. The resulting final mixture is then ignited at the burner head, typically comprising one or more long narrow slots. The flame thus produced will cause at least a certain proportion of the element of interest (typically a metal originally present in the form of a chemical compound dissolved in a solvent) to be reduced to its atomic state. The amount of absorption of monochromatic radiation (at a resonant spectral line of the element in its atomic state) measured by the atomic absorption spectrophotometer is proportional to the amount (or concentration) of the element of interest in the original sample solution at 59, which of course will be constantly supplied through the capillary tube (from end 57 to tip 51).

Heretofore it was believed that the liquid-supplying tip of the metallic needle, corresponding in position to the tip 51 of the continuous capillary tube, had to be precisely concentric to the venturi throat 26 (see, for example, the aofrementioned Davies et al article at page 817, left column, lines 3–8). Contrary to such expectations, it has been discovered and established that the relatively flexible tip 51 operates just as efficiently as the originally used rigid needle. This unexpected result is believed to be due to two factors, namely, that perfect concentricity is not required for optimum results, and that the rapidly moving gaseous stream within throat 26 tends to at least partially center tip 51 therein. Since the material of both capillary 50 (and therefore of course, its continuous tip 51, as well as its continuously extending sample supply portion 56, 57) and the venturi member 11 are corrosive-resistant artificial resins, the nebulizer of the present invention may be utilized directly with corrosive (e.g., acidic) sample solutions (even, gold in aqua regia) without danger of corroding these parts or contaminating the sample solution by dissolving at least some metals from the previously utilized materials (e.g., stainless steel) of the previously utilized metal needle and metal venturi member. Thus, the device not only has a longer use life, but the possibility of adding spurious signals caused by such dissolved metal is avoided. Additionally the continuous nature of the tube from end 57 to tip 51 avoids the previously experienced difficulty of forming deposits from concentrated sample solutions at the (necessarily changing in effective internal diameter) junction of the capillary tubing and metal needle previously utilized. Additionally, such previously necessary connection between the metal needle and the surrounding flexible capillary tubing often caused splitting of the wall of the tubing (which surrounds the needle). When this splitting did not occur through the entire thickness of the tubing wall, it was difficult to detect visually, but nevertheless could cause erroneous and often erratic behavior of the absorption signal of the atomic absorption spectrometer, because of the variance in the quantity of nebulized sample solution actually introduced.

I claim:

1. In a nebulizer for forming a fine spray or mist from an originally liquid (sample) solution of the type including means for forming a venturi restriction including a narrow venturi throat through which a gas travels at accelerated velocity, and a nebulizing tube of substantially capillary size positioned with its tip within the narrow venturi throat, through which tube the sample solution is introduced and caused to nebulize into a fine mist at its tip by means of the high velocity gas flow through the narrow venturi throat in the vicinity of said tip so as to form a mixture of fine liquid mist and gas, the improvement comprising:

said liquid nebulizing tube being in the form of a flexible monolithic corrosion-resistant artificial resin tubing, one end of which forms said nebulizing tip of said tube, while the other remote end is directly introduced into a container holding the original liquid sample solution.

2. An improved nebulizer according to claim 1, in which:

at least that part of said means for forming said narrow venturi throat which comes into contact with the nebulized sample solution mist comprises also a corrosion-resistant artificial resin.

3. An improved nebulizer according to claim 1, in which:

means defining a widening opening communicating with said venturi throat in the direction of movement of the fine mist and gas mixture are provided to directionally diffuse said mixture;

and at least that part of said opening defining means contacted by said mixture is also of a corrosion-resistant artificial resin.

4. An improved nebulizer according to claim 1, in which:

longitudinally adjustable means are provided for holding said continuous corrosion-resistant tubing;

said holding means comprises means made of an artificial resin defining a tubular internal channel through which said tubing passes;

and a bonding material securely attaches at least part of the exterior surface of said tubing to at least part of said means defining said tubular internal channel.

* * * * *